US006485949B1

(12) United States Patent
Piazza et al.

(10) Patent No.: US 6,485,949 B1
(45) Date of Patent: Nov. 26, 2002

(54) EPOXIDATION OF CARBON-CARBON DOUBLE BOND WITH MEMBRANE BOUND PEROXYGENASE

(75) Inventors: George J. Piazza, Meadowbrook, PA (US); Alberto Nunez, Dresher, PA (US); Thomas A. Foglia, Lafayette Hill, PA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 20 days.

(21) Appl. No.: 09/772,301

(22) Filed: Jan. 29, 2001

(51) Int. Cl.$^7$ .......................... C12N 11/08; C12P 17/02
(52) U.S. Cl. ........................................ 435/180; 435/123
(58) Field of Search ........................................ 435/180

(56) References Cited

U.S. PATENT DOCUMENTS

| | | | |
|---|---|---|---|
| 5,354,875 A | 10/1994 | Nemeth et al. | |
| 5,620,938 A | 4/1997 | Sielcken | |
| 5,780,655 A | 7/1998 | Shum | |
| 6,160,138 A | 12/2000 | Escrig et al. | |

OTHER PUBLICATIONS

Ratledge, C., "Biotechnology Techniques", *Biotechnology Letters*, vol. 22 (3), Feb. 1, 2000.
Piazza, G., et al., "Immobilized Peroxygenase for the Production of Epoxy Fatty Acids", *91$^{st}$ AOCS Annual Meeting & Expo. Abstract*, Apr. 25, 2000.
Piazza, G., et al., "Epoxidation of Fatty Acids With Membrane–Supported Peroxygenase", *Biotechnology Letters*, vol. 22, pp. 217–221, 2000.
Soucek, M., "Corrosion Resistant Ceramers Using Soybean Oil and Epoxidized Soybean Oil", *Corrosion Resistant Ceramers*, North Dakota Soybean Council Oct. 23, 2000.
Piazza, G., et al., "Enantioselective Formation of an α, β–Epoxy Alcohol by Reaction of Methyl 13(S)–Hydroperoxy–9(Z), 11(E)–Octadecadienoate with Titanium Isopropoxide", *JAOCS*, vol. 74, (11), pp. 1385–1390, 1997.
Blee, E., et al., "Efficient Expoxidation of Unsaturated Fatty Acids by a Hydroperoxide–Dependent Oxygenase", *J. Biol. Chem.*, vol. 265, (22), pp. 12887–12894, 1990.

Piazza, G., et al., "Preparation of Fatty Epoxy Alcohols Using Oat Seed Peroxygenase in Nonaqueous Media", *JAOCS*, vol. 76, (5), pp. 551–555, 1999.
Blee, E., "Phytooxylipins: The Peroxygenase Pathway", *Lipoxygenase and Lipoxygenase Pathway Enzymes*. Chapter 8, pp. 138–161, 1996.
Piazza, G., "Some Recent Advances in Epoxide Synthesis", *Recent Developments in the Synthesis of Fatty Acid Derivatives*, Chapter 11, pp. 182–195, 1999.
Hamberg, M., et al., "Hydroperoxide–Dependent Eposidation of Unsaturated Fatty Acids in the Broad Bean (Vicia faba L.)", *Archives of Biochem. and Biophys.*, vol. 283, (2), pp. 409–416, 1990.
Blee, E., et al., "Mechanism of Reaction of Fatty Acid Hydroperoxides With Soybean Peroxygenase", *J. Biol. Chem.*, vol. 268, (3), pp. 1708–1715, 1993.
Hamberg, M., et al., "Peroxygenase–Catalyzed Fatty Acid Epoxidation in Cereal", *Plant Physiology*, vol. 110, (12), pp. 807–815, 1996.
Hamberg, M., et al., "On the Specificity of Fatty Acid Epoxygenase in Broad Bean (*Vicia faba L.*)", *Plant Physiol.*, vol. 99, pp. 987–995, 1992.
Gan, L.H., et al., "Kinetic Studies of Epoxidation and Oxirane Cleavage of Palm Olein Methyl Esters", *JAOCS*, vol. 69, (4), pp. 347–351, Apr. 1992.
Carlson, K.D., et al., "Chemical Epoxidation of a Natural Unsaturated Epoxy Seed Oil from *Vernonia galamensis* and a Look at Epoxy Oil Markets", *JAOCS*, vol. 62, (5), pp. 934–939, May 1985.

*Primary Examiner*—Herbert J. Lilling
(74) *Attorney, Agent, or Firm*—M. Howard Silverstein; John D. Fado; G. Byron Stover

(57) ABSTRACT

A method has been discovered for the epoxidation of a compound having at least one carbon-carbon double bond, the method involves reacting a compound having at least one carbon-carbon double bond, a solvent, an oxidant, and membrane bound peroxygenase. Also discovered is a method for preparing the membrane bound peroxygenase involving grinding seeds containing peroxygenase to produce ground seeds, homogenizing the ground seeds in a buffer to form a slurry, centrifuging the slurry to produce a first supernatant, centrifuging the first supernatant to produce a second supernatant, and filtering said second supernatant through a protein-binding membrane filter to produce membrane bound peroxygenase; optionally the second supernatant is filtered through a hydrophilic membrane filter prior to filtering the second supernatant through a protein-binding membrane filter.

8 Claims, 5 Drawing Sheets

EPOXIDATION OF CARBON-CARBON DOUBLE BOND WITH MEMBRANE BOUND PEROXYGENASE

BACKGROUND OF THE INVENTION

The present invention relates to a method for the epoxidation of a compound having at least one carbon-carbon double bond, the method involves reacting a compound having at least one carbon-carbon double bond, a solvent, an oxidant, and membrane bound peroxygenase. The present invention also relates to a method for preparing the membrane bound peroxygenase involving grinding seeds containing peroxygenase to produce ground seeds, homogenizing the ground seeds in a buffer to form a slurry, centrifuging the slurry to produce a first supernatant, centrifuging the first supernatant to produce a second supernatant, and filtering said second supernatant through a protein-binding membrane filter to produce membrane bound peroxygenase; optionally the second supernatant is filtered through a hydrophilic membrane filter prior to filtering the second supernatant through the protein-binding membrane filter.

Fats and oils (e.g., soybean oil and the esters of tall oil fatty acids) are renewable materials that are used as feed stocks for the production of industrial materials such as paints, varnishes, emulsifiers, and lubricants. To achieve a formulation with the desired properties, it is usually necessary to chemically modify the fat or oil. For unsaturated fats and oils, one common modification is epoxidation which leads to a material with increased polarity and enhanced reactivity (Carlson, K. D., et al., J. Am. Oil Chem. Soc., 62: 934–939 (1985); Piazza, G. J., Some Recent Advances in Epoxide Synthesis, IN Recent Developments in the Synthesis of Fatty Acid Derivatives, edited by G. Knothe and J. T. P. Derksen, AOCS Press, Champaign, 1999, pp. 182–195)). Epoxidized oils are used as plasticizers and are generated on an industrial scale using peracids (Gan, L. H., et al., J. Am. Oil Chem. Soc., 69: 347–351 (1992)). The latter are generated by reacting formic or acetic acid with hydrogen peroxide in the presence of a strong acid catalyst. A disadvantage of this procedure is that the strong acid catalyzes epoxide ring opening, causes equipment corrosion, and it must be recycled or neutralized before discharge into the environment. Also the peracid intermediate is unstable, and explosive conditions are possible.

The use of enzymes offers the possibility of developing an environmentally benign and more selective epoxidation reaction. One enzyme that might be useful for this purpose is termed peroxygenase. This enzyme catalyzes the heterolytic cleavage of a peroxygen bond and transfers the liberated oxygen to an oxidizable functional group, such as a carbon-carbon double bond, to give an epoxide product. Thus, in the presence of organic hydroperoxide, oleic acid 1 is converted to the 9,10-epoxide 2 by peroxygenase isolated from soybean, broad bean, and oat (FIG. 1) (Hamberg, M., et al., Arch. Biochem. Biophys., 283: 409–416 (1990); Hamberg, M., et al., Plant Physiol., 110: 807–815 (1996); Hamberg, M., et al., Plant. Physiol., 99: 987–995 (1992); Blée, E., et al., J. Biol. Chem., 268: 1708–1715 (1993); Blée, E., Phytooxylipins: The Peroxygenase Pathway, IN Lipoxygenase and Lipoxygenase Pathway Enzymes, edited by G. J. Piazza, AOCS Press, Champaign, 1996, pp. 138–161)). Similarly linoleic acid afforded the 9,10-and 12,13-epoxy derivatives. Studies with peroxygenase from soybean and broad bean show that cis-double bonds are the preferred substrates of peroxygenase (Hamberg, M., et al., Plant. Physiol., 99: 987–995 (1992); Blée, E., et al., J. Biol. Chem., 265: 12887–12894 (1990)). Peroxygenase can also catalyze internal epoxidation if the peroxygen group is contained in a molecule with a double bond. Thus when the peroxygenases from soybean and broad bean were presented with the enzymatically-generated hydroperoxide of linoleic acid 3 (13(S)-hydroperoxy-9(Z),11(E)-octadecadienoic acid, HPODE), products were 13(S)-hydroxy-9(Z),11(E)-octadecadienoic acid 4 and 9,10-epoxy-13(S)-hydroxy-11 (E)-octadecenoic acid 5 (Hamberg, M., et al., Biochem. Biophys., 283: 409–416 (1990); Hamberg, M., et al., Arch. Biochem. Biophys., 283: 409–416 (1990); Blée, E., et al., J. Biol. Chem., 268:1708–1715 (1993); Piazza, G. J., et al., J. Am. Oil Chem. Soc., 76: 551–555 (1999)). Recently it has been demonstrated that a peroxygenase from oat seeds can catalyze the epoxidation of oleic acid using hydrogen peroxide as the oxygen donor (Hamberg, M., et al., Plant Physiol., 110: 807–815 (1996)).

Traditional methods for using an enzyme for synthesis require two separate steps: isolation/purification of the enzyme from its biological source and chemical or physical immobilization. In the study described herein, a simple, rapid method for immobilizing oat seed peroxygenase on filter membranes is described. The activity and reusability of the immobilized peroxygenase preparation also was investigated, and the pH and temperature dependence of epoxidation by membrane-bound peroxygenase was examined to determine optimal reaction conditions.

SUMMARY OF THE INVENTION

In accordance with the present invention there is provided a method for the epoxidation of a compound having at least one carbon-carbon double bond, the method involves reacting a compound having at least one carbon-carbon double bond, a solvent, an oxidant, and membrane bound peroxygenase. There is also provided a method for preparing the membrane bound peroxygenase involving grinding seeds containing peroxygenase to produce ground seeds, homogenizing the ground seeds in a buffer to form a slurry, centrifuging the slurry to produce a first supernatant, centrifuging the first supernatant to produce a second supernatant, and filtering said second supernatant through a protein-binding membrane filter to produce membrane bound peroxygenase; optionally the second supernatant is filtered through a hydrophilic membrane filter prior to filtering the second supernatant through the protein-binding membrane filter.

DETAILED DESCRIPTION OF THE INVENTION

Figure 1:
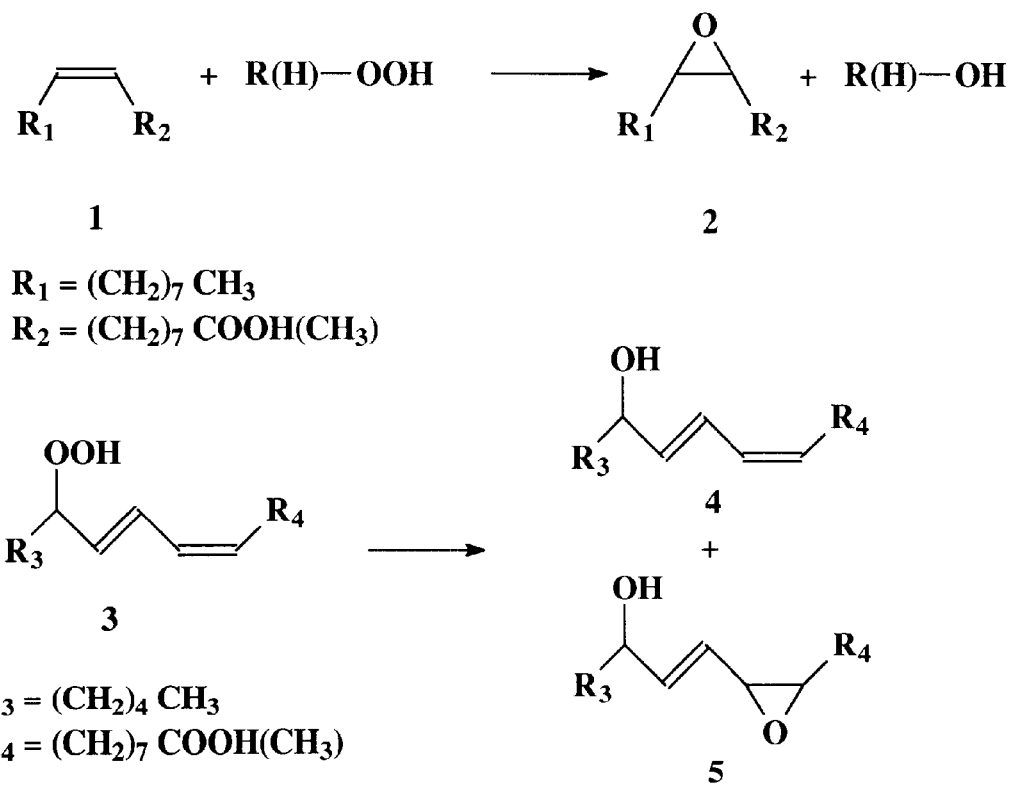
FIG. 1 shows two reactions catalyzed by peroxygenase; Top: formation of epoxide 2 with externally added hydroperoxide, Bottom: peroxygenase cleavage of fatty acid hydroperoxide 3 with and without inter-or intramolecular oxygen transfer to form alcohol 4 and epoxy alcohol 5.

A method is disclosed for the epoxidation of a compound having at least one carbon-carbon double bond. It is expected that the method may be used for the epoxidation of any compound having at least one carbon-carbon double bond; examples of such compounds (e.g., olefinic compounds) are found in the following U.S. Patents (which are incorporated by reference in their entirety): U.S. Pat. Nos. 6,160,138; 5,780,655; 5,620,938; 5,354,875. The compound having a carbon-carbon double bond generally includes alkenes (e.g., $C_nH_{2n}$ where n is two to about 100, preferably n is two to about 20, more preferably n is about six to about 18; preferably the cis stereoisomers of the alkenes), the above alkenes that are substituted (e.g., R—CH=C—R' where R and R' are an aromatic or aliphatic organic compound such as —$C_6H_5$, —$C_2H_5$, —$C_3H_7$; R and R' may also contain a heteroatom substituent such as —$C_3H_6$X where X is OH, Cl, F, Br, $NH_2$, SH, or COOH, or —$C_3H_5$X where X is O or NH; R and R' may be the same or different), compounds having more than one carbon-carbon double bond (e.g., R—$CH_2$(CH=CH)$_x$($CH_2$)$_y$CH=CHCH$_2$R' where x is one to about 100 (preferably one to about 20, more preferably one to about five), where y is zero to about 100 (preferably zero to about 14, more preferably zero to about three), R and R' are as defined above or may also be H), unsaturated fatty acids (e.g., oleic acid, linoleic acid, myristoleic acid, palmitoleic acid, vaccenic acid, ricinoleic acid, conjugated linoleic acid, linolenic acid, gamma linolenic acid, eicosenoic acid, eicosadienoic acid, eicosatrienoic acid, arachidonic acid, erucic acid, brassidic acid, docosahexaenoic acid), and derivatives of unsaturated fatty acids (e.g., ester derivatives such as methyl oleate, ethyl oleate, isopropyl oleate, lauryl oleate, myristyl oleate, palmityl oleate, stearyl oleate, methyl linoleate, ethyl linoleate, isopropyl linoleate, lauryl linoleiate, myristyl linoleate, palmityl linoleate, stearyl linoleate, methylated 13(S)-hydroperoxy-9(Z),11(E)-octadecadienoate; amide derivatives such as oleamide, linoleamide, methyl oleamide, methyl linoleamide, ethyl oleamide, ethyl linoleamide, lauryl oleamide, lauryl linoleamide, myristyl oleamide, myristyl linoleamide, palmityl oleamide, palmityl linoleamide, oleayl oleamide, oleayl linoleamide). The present invention may be used to produce ethylene oxide, propylene oxide, and epichlorohydrin. Preferred compounds having at least one carbon-carbon double bond include those with cis double bonds (e.g., those described in U.S. Pat. No. 6,160, 138 where either $R_1$ and $R_3$ or $R_2$ and $R_4$ are hydrogen), terminal double bonds (e.g., styrene), and those with a cyclic structure (e.g., those described in U.S. Pat. No. 6,160,138).

The method involves reacting a compound having at least one carbon-carbon double bond and membrane bound peroxygenase in the presence of a solvent and an oxidant. The solvent may be an aqueous solvent composed of a buffer having a pH from about 4.5 to about 9.5 (preferably a pH from about 5 to about 9) such as aqueous phosphate buffer/ Tween or water with a manual or automatic monitoring system that detects and adjusts the pH or hydrogen ion concentration; the solvent may be a nonpolar solvent such as heptane, isooctane, dichloromethane, or toluene. The reaction time is about one minute up to about seven days (preferably about two hours to about 24 hours, more preferably about six hours to about 12 hours). The reaction temperature is about 5° C. to about 75° C. (preferably about 15° C. to about 65° C., more preferably about 15° C. to about 35° C.). The oxidant is generally an organic hydroperoxide such as t-butyl hydroperoxide or hydrogen peroxide; examples of oxidants include t-butyl hydroperoxide (max yield at pH 7.5–8.0), cumene hydroperoxide, hydrogen peroxide (max yield at pH 5.5), and urea-hydrogen peroxide complex. Generally, the oxidant is added in steps instead of all at once since it was found that the addition of large amounts of some oxidizing agents tends to diminish the activity of peroxygenase. A convenient method is to add (generally manually) 20 mol % of the oxidant every one or two hours; an automatic addition of small amounts of oxidant more frequently is possible. If the oxidant is found to be toxic to the peroxygenase enzyme activity, then the oxidant may be added even more slowly to insure that its concentration in the reaction medium remains low. As the reaction progresses, the rate of conversion of starting material to product slows, and the oxidant may be added less frequently, or alternatively if automatic addition is used then the oxidant may be added more slowly. The total amount of oxidant added to achieve maximum conversion to epoxide is 140 to 290 mole % of starting material, although for some applications incomplete conversion to epoxide is desirable (in which case less oxidant is added).

One unexpected advantage of the present invention is the ease in isolating the epoxidized compound. At the end of the epoxidation reaction, the reaction medium is physically separated from the membrane-bound peroxygenase. This is achieved in the laboratory by decanting the reaction medium from the membranes, and then washing the membranes with diethyl ether to remove traces of epoxide from the membranes. If the reaction medium is an organic solvent such as heptane, the organic solvent and diethyl ether wash are combined and then removed by evaporation to give the epoxide product. If the reaction medium is aqueous and a fatty acid is used as the starting material, the reaction medium is treated with dilute hydrochloric acid to give pH 3.0. The acidified medium is extracted with diethyl ether. The diethyl ether extract and the diethyl ether fraction from the membrane wash are combined and evaporated to give the epoxide product. If the reaction medium is aqueous and the ester of a fatty acid is used as the starting material or the starting material consists of a substance that contains no carboxylic acid, such as cyclohexene or styrene, then the acidification step is omitted.

The membrane bound peroxygenase is produced by a method involving grinding seeds (e.g., oat, soybean, broad bean) containing peroxygenase, generally for about 20 to about 60 seconds, to produce ground seeds; homogenizing the ground seeds in a buffer (generally a buffer having a pH near 7 (e.g., about 6.5 to about 7.5), specifically 0.1 M potassium phosphate having a pH of 6.7) to form a slurry, generally homogenizing involves blending for about one to about two minutes; centrifuging the slurry to produce a first supernatant, generally at about 9,000 to about 16,000×g for about 10 to about 15 min.; centrifuging the first supernatant to produce a second supernatant, generally at about 9,000 to about 16,000×g for about 10 to about 15 min.; and filtering the second supernatant through a protein-binding membrane filter to produce membrane bound peroxygenase. The protein-binding membrane filter must have a relatively small pore size (about 0.1 to about 2 $\mu$m, preferably about 0.2 to about 1 $\mu$m) in order to effectively hold the peroxygenase enzyme; this is extremely important since it was not predictable that the enzyme would be held onto this type of membrane, that it would be active on this membrane, and that it would not "wash" off of this membrane when the membrane was added to an aqueous reaction mixture. Generally the protein-binding membrane filter includes Nylon 66 (0.2 $\mu$m) and hydrophobic membranes such as Fluoropore (polytetrafluoroethylene (PTFE); 0.2 $\mu$m) and Durapore (0.22 $\mu$m) membrane filters. Optionally the second supernatant is prefiltered through a hydrophilic membrane filter prior to filtering the second supernatant through the protein-binding membrane filter. Generally the hydrophilic membrane filter will filter out the extraneous matter without holding onto the desired peroxygenase activity; the necessary pore size of such hydrophilic membrane filters is easily determined by one skilled in the art. Such hydrophilic (water-loving or polar) membranes include Durapore (polyvinylidiene fluoride (PVDF)).

The following examples are intended only to further illustrate the invention and are not intended to limit the scope of the invention as defined by the claims.

EXAMPLES

Oat seeds (Avena sativa L.) were supplied by Equine Speciality Feed Co. (Ada, Minn.). Durapore (PVDF, hydrophilic) membranes and Fluoropore (PTFE, hydrophobic) membranes were from Millipore (Bedford, Mass.). Sodium oleate was purchased from Nu-Chek-Prep, Inc. (Elysian, Minn.). Heptane and hydrogen peroxide (30%) were purchased from Aldrich (Milwaukee, Wis.). Sigma (St. Louis, Mo.) was the source of t-butyl hydroperoxide (70%). Water was purified to a resistance of 18 m$\Omega$-cm using a Bamstead (Dubuque, Iowa) NANO pure system. All other reagents were of the highest purity available. Preparation of 3 methyl 13(S)-hydroperoxy-9(Z),11 (E)-octadecadienoate (Me-HPODE): Linoleic acid was enzymatically converted to HPODE using lipoxygenase as described previously (Piazza, G. J., et al., J. Am. Oil Chem. Soc., 74: 1385–1390 (1997)) and HPODE was methylated with $CH_2N_2$ to give Me-HPODE.

Preparation of oat seed microsomes (membrane-bound peroxygenase): For small scale reactions, dry oat seeds (10 g) were ground in 5 g batches in a 37 mL Waring Blender (New Hartfod, Conn.) mini-jar for 30 s. The ground oat seeds were transferred to a 110 mL mini-jar containing 90 mL cold 0.1 M potassium phosphate buffer (pH 6.7) and blended for 90 s at high speed. The oat seed slurry was centrifuged at 9000×g for 10 min. The pellet was discarded and the supernatant was centrifuged for an additional 10 min at 9000×g. After the second centrifugation, the pellet was discarded and the supernatant was divided into four equal portions and each portion was subjected to vacuum infiltration with a Fluoropore membrane (0.2 $\mu$m, 47 mm). The Fluoropore membrane was wetted with methanol before loading onto the membrane holder. After vacuum infiltration, the membrane was cut into four equal size pieces, and these pieces placed into a reaction flask.

For large scale reactions 100 g of oat were ground dry (30 s), and then the ground seeds were homogenized in 900 mL of cold 0.1 M potassium phosphate buffer (pH 6.7) using a Waring commercial blender (2 min). The slurry was centrifuged at 16,000×g for 15 min. The pellet was discarded and the supernatant was centrifuged for an additional 15 min at 16,000×g. The supernatant was passed through a hydrophilic Durapore membrane filter (0.65 $\mu$m, 142 mm), and the filtrate was collected and divided into quarters and each was passed through a hydrophobic Fluoropore membrane (0.2 $\mu$m, 142 mm).

Epoxidation reactions: The indicated amount of Me-HPODE, oleic acid, or elaidic acid dissolved in $CH_2Cl_2$ was added to a 10 or 15 mL stoppered Erlenmeyer flask, and the solvent removed under a stream of nitrogen. Into each flask was added water-saturated heptane or 0.1 M potassium phosphate buffer (pH 6.7) containing 0.1% (w/v) Tween 20 and the membrane pieces. The reaction was initiated by adding t-butyl hydroperoxide. The suspension was agitated at 20° C. for 2 h or as indicated. At the end of the incubation period, 3.5 mL methanol was added, and after removal of the membrane pieces, the contents were transferred to a 125 mL separatory funnel. The products were partitioned between 30 mL diethyl ether and 25 mL water. After separating the layers, the water layer was extracted with 25 mL diethyl ether. The ether fractions were combined, dried over sodium sulfate, and taken to dryness under a stream of nitrogen. The products were dissolved in 2 mL dichloromethane and stored at −20° C. until analysis. When fatty acid was the substrate, the products were methylated with $CH_2N_2$ before analysis.

Epoxidations: Smaller scale reactions, used for determining pH and temperature profiles, contained 5 mg (16.4 $\mu$mol) sodium oleate, 6.3 mL buffer, 0.7 mL 1% (w/v) Tween 20, and 7.3 $\mu$mol t-butyl hydroperoxide or $H_2O_2$. The buffer consisted of four components, each with a different pKa, to provide buffering capacity over a broad pH range. Each component was present at a concentration of 50 mM. The components were tricine (N-tris(hydroxymethyl)-methylglycine), MES (2-(N-morpholino)ethanesulfonic acid), HEPES (N-(2-hydroxyethyl)piperazine-N'-(2-ethanesulfonic acid)), and glacial acetic acid. Each assay was agitated at 20° C. for 1 h or as indicated. Larger scale reactions contained 100 mg (0.329 mmol) sodium oleate, and 32.4 mL buffer. The buffer consisted of 50 mM HEPES/ 0.1% (w/v) Tween 20, pH 7.5, for reactions using t-butyl hydroperoxide or 50 mM MES/50 mM glacial acetic acid/ 0.1% (w/v) Tween 20, pH 5.5, for reactions using hydrogen peroxide. Products were extracted and analyzed by HPLC (Piazza, G. J., et al., Biotech. Lett., 22: 217–221 (2000)) as described below.

High performance liquid chromatography (HPLC): Reaction products were separated on a Lichrosorb 5$\mu$ diol HPLC column (250×10 mm) (Phenomenex, Torrance, Calif.) installed on a Waters (Milford, Mass.) LCM1 HPLC instrument. The instrument was equipped with a Waters 996 photodiode array detector in tandem with a Varex evaporative light-scattering detector MK III (Alltech, Deerfield, Ill.) operated at a temperature of 55° C., and with $N_2$ as the nebulizing gas at a flow rate of 1.5 L/min. Mobile phase composition and gradient was hexane: isopropanol (97:3) to (94:6) over 29 min using a linear gradient. The flow rate was 2 mL/min.

Gas chromatography-mass spectrometry (GC-MS): Mass spectra were obtained on a Hewlett Packard (HP) (Wilmington, Del.) 5890 Series II Plus gas chromatograph equipped with a HP 5972 mass selective detector set to scan from m/e 45 to 400 at 2 scans per s. A capillary column (Supelco SP-2340, 60 m×0.25 mm) coated with 0.20 μm poly(biscyanopropylsiloxane) was used to separate the products. The oven temperature was increased from 130° C. to 177° C. at 2° C. per min and held at 177° C. for 5 min; increased to 230° C. at 10° C. per min and held at 230° C. for 15 min; increased to 250° C. at 10° C. per min and held at 250° C. for 10 min. The injector port temperature was 250° C., and the detector transfer line temperature was 250° C.

Figure 2:
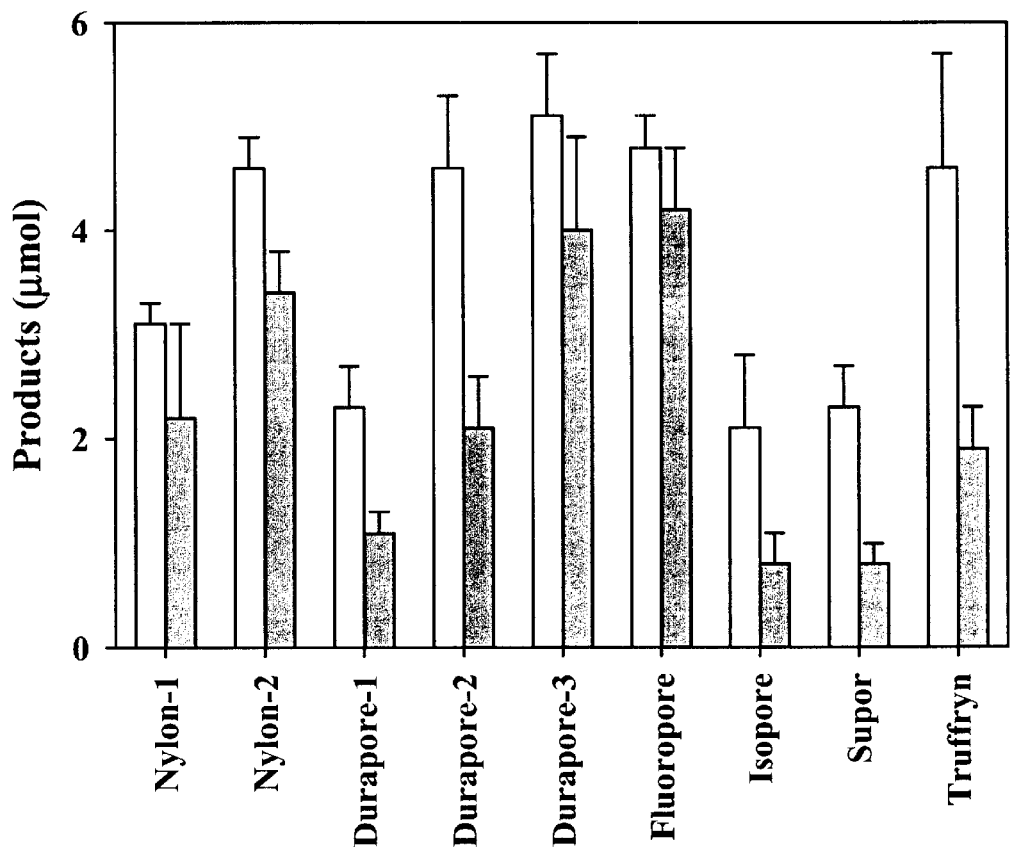
FIG. 2 shows an assay in heptane on compound 3 in FIG. 1 of peroxygenase residing on different membranes. Colorless bars, alcohol 4 (methyl 13(S)-hydroxy-9(Z),11(E)-octadecadienoate); cross hatch bars, epoxy alcohol 5 (methyl cis-9,10-epoxy-13(S)-hydroxy-11(E)-octadecenoate). Values are the mean ±SE, n=3-6. Nylon-1: Nylon 66, 0.45 μm; Nylon-2: Nylon 66,0.2 μm; Durapore-1: Durapore, 0.22 μm; Durapore-2: Durapore, 0.1 μm; Durapore-3: Durapore hydrophobic, 0.22 μm. Other membranes were as described below. Each assay also contained Me-HPODE (10 mg) and 0.7 mL water-saturated heptane.

Oat seeds were homogenized in buffer, and after two low speed centrifugations, the resulting supernatant was passed through filter papers or membranes. The amount of peroxygenase activity retained on the filter papers or membranes was determined by measuring the conversion of hydroperoxide 3 to products 4 and 5 by HPLC (FIG. 1). No activity was observed with Whatman paper filters tested whereas all tested membranes showed some retained peroxygenase activity (FIG. 2). With each membrane, more alcohol 4 formed than epoxy alcohol 5. The highest levels of 5 were obtained with the Durapore and Fluoropore membranes which are both hydrophobic. Further experimentation was performed only with the Fluoropore membrane.

As shown in FIG. 2, an unsaturated substrate can be converted to an epoxide by peroxygenase when an appropriate oxidant is present. Table 1 lists the results obtained with four different oxidants used on oleic acid. When aqueous phosphate buffer/Tween was the solvent, t-butyl hydroperoxide and cumene hydroperoxide gave better yields of epoxide than hydrogen peroxide or its urea adduct. A similar finding was obtained in the solvent heptane except that the overall yields of epoxide were somewhat lower. Contol experiments with the oxidants, oleic acid, and Fluoropore membranes showed that no epoxide was formed without the addition of the oat seed fraction.

TABLE 1

Influence of solvent and oxidant on the epoxidation of oleic acid by peroxygenase bound on a Fluoropore membrane.

| | Epoxide (μmol)[a] (% yield of epoxide) | |
|---|---|---|
| Oxidant | Aqueous[b] | Heptane[c] |
| t-Butyl Hydroperoxide | 2.8 (79%) | 1.8 (51%) |
| Cumene Hydroperoxide | 2.0 (56%) | 1.6 (45%) |
| Hydrogen Peroxide | 0.6 (17%) | 0.6 (17%) |
| Urea-Hydrogen Peroxide | 0.7 (20%) | 0.5 (14%) |

[a]Assays were conducted for 2 h at 20° C. and contained 1 mg (3.54 μmol) oleic acid and 28.3 μmol oxidant; results are an average of two determinations.
[b]Buffer/Tween (0.7 mL).
[c]Water-saturated heptane (0.7 mL).

To ascertain whether membrane-bound peroxygenase is reusable, it is necessary to conduct repeat batch epoxidations. Table 2 shows the conversion of oleic acid to epoxide upon reuse of peroxygenase immobilized on a Fluoropore membrane. In the first cycle higher amounts of epoxide were obtained in buffer/Tween than in heptane, as before. In the second and third cycles lower amounts of epoxide were obtained, but in buffer/Tween and heptane the membrane preparation retained a considerable amount of its initial activity. By the third use, the amount of epoxide obtained was reduced by only 17% in buffer/Tween and 38% in heptane. The very fact that Fluoropore-bound peroxygenase retained its activity through three cycles in buffer/Tween demonstrates that peroxygenase is not easily "washed" off. This was a surprising result given that peroxygenase was initially solubilized in aqueous buffer. Without being bound by theory, the fact that peroxygenase was not washed off must indicate a strong degree of interaction between peroxygenase and the membrane.

TABLE 2

Reuse of peroxygenase bound on Fluoropore membrane for epoxidation of oleic acid with t-butyl hydroperoxide.

| | Epoxide (μmol)[a] (% yield of epoxide) | |
|---|---|---|
| Cycle | Aqueous[b] | Heptane[c] |
| 1 | 2.9 (82%) | 1.6 (45%) |
| 2 | 2.7 (76%) | 1.4 (40%) |
| 3 | 2.4 (68%) | 1.0 (28%) |

[a]Assays were conducted at for 2 h at 20° C. and contained 1 mg (3.54 μmol) oleic acid and 28.3 μmol t-butyl hydroperoxide; results are an average of two determinations.
[b]Buffer/Tween (0.7 mL).
[c]Water-saturated heptane (0.7 mL).

Figure 3:
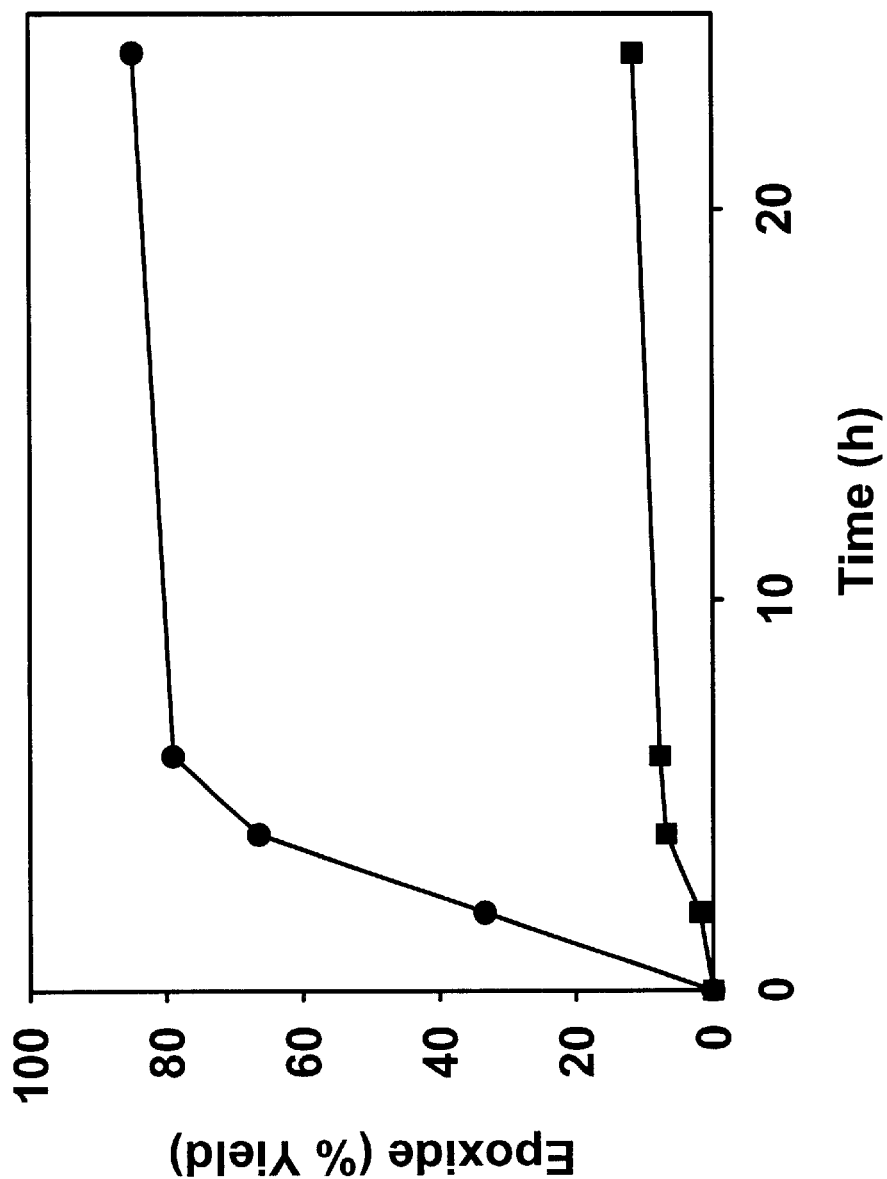
FIG. 3 shows the time course of epoxidation of oleic and elaidic acids by peroxygenase bound on a Fluoropore membrane. Assays contained 5 mg (17.7 μmol) oleic acid (●) or elaidic acid (■) and 7.0 mL buffer/Tween. At t=0, 1, 2, and 4 h, 7.3 μmol t-butyl hydroperoxide was added. At t=6 h, 21.9 μmol t-butyl hydroperoxide was added.

When the amounts of oleic acid substrate and t-butyl hydroperoxide oxidant were increased leaving the level of peroxygenase immobilized on a Fluoropore membrane unchanged, the percent yield of the epoxide of oleic acid decreased. For example from Tables 1 and 2, the percent yield of epoxide obtained in aqueous buffer is approximately 80%. When the level of oleic acid and t-butyl hydroperoxide were increased five-fold, the percent yield of epoxide was reduced to approximately 60% even though the reaction time was increased from two h to twenty-four h. It was assumed that peroxygenase was deactivated by t-butyl hydroperoxide, as deactivation by $H_2O_2$ and HPODE has previously been reported (Hamberg & Hamberg 1990b; 1992), Arch. Biochem. Biophys. 283: 409–416 (1990) and Hanburg et al. Plant Physiol. 99: 987–995 (1992). It was hypothesized that if smaller amounts of t-butyl hydroperoxide were added several times over a longer time period, peroxygenase deactivation might be reduced. This was found to be the case. As shown in FIG. 3, when smaller amounts of t-butyl hydroperoxide were added over a 4 h period, 85% of oleic acid was converted to its epoxide at 24 h.

When experiments were performed with elaidic acid, the trans analogue of oleic acid, the yield of epoxide was relatively low. At 24 h only 11% of elaidic acid was converted to its epoxide (FIG. 3). Discrimination against trans double bonds has been previously reported for peroxygenase isolated from soybean and broad bean (Hamberg, M., et al., Plant Physiol., 99: 987–995 (1992); Blée, E., et al., J. Biol. Chem., 265: 12887–12894 (1990)).

Thus a method for the isolation of peroxygenase has been devised. The peroxygenase preparation is reusable to a degree and can be used to convert double bonds to epoxides. Although the example above emphasized the use of lipid substrates, it is expected that peroxygenase can be a usefull catalyst for epoxide formation in a wide variety of chemical substances. It is particularly useful in those situations requiring the absence of an acidic catalyst or those in which the selective epoxidation of a cis double bond is required.

Figure 4:
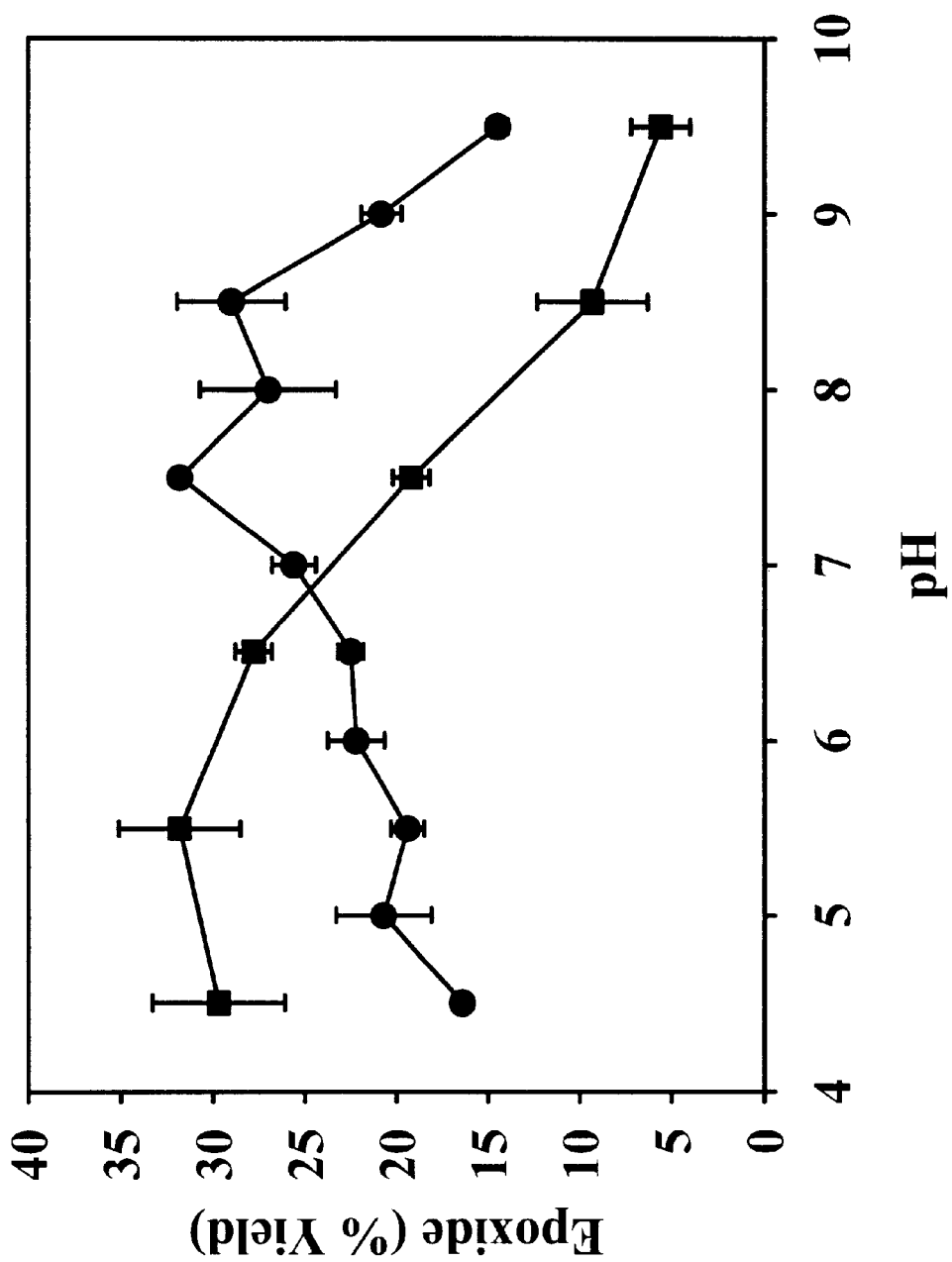
FIG. 4 shows the effect of pH on the epoxidation of sodium oleate by peroxygenase bound on a Fluoropore membrane. Assays contained 5 mg (16.4 μmol), 6.3 ml buffer, 0.7 ml 1% (w/v) Tween 20, and 7.3 μmol t-butyl hydroperoxide (●) or $H_2O_2$ (■). Assays were conducted for 1 h at 20° C. Percent yield calculations based on sodium oleate (theoretical maximum 44%). Each data point is the average of four to six repetitions.

Optimizing reaction parameters: Before proceeding to larger scale reactions, it was necessary to determine reaction conditions that promoted the most rapid rate of epoxide formation. To accomplish this, reaction time was restricted to 1 h and suboptimal (less than stoichiometric) quantities of oxidant added, as prior work indicated that higher oxidant levels deactivate peroxygenase (11–13). FIG. 4 shows the affect of buffer pH on the yield of epoxide formed from sodium oleate in one h. The highest yield of epoxide was obtained with t-butyl hydroperoxide at pH 7.5–8.0. Hydrogen peroxide gave the highest yield of epoxide at pH 5.5. Note however that the yield of epoxide was approximately identical for both t-butyl hydroperoxide and hydrogen peroxide at their pH optima.

Figure 5:
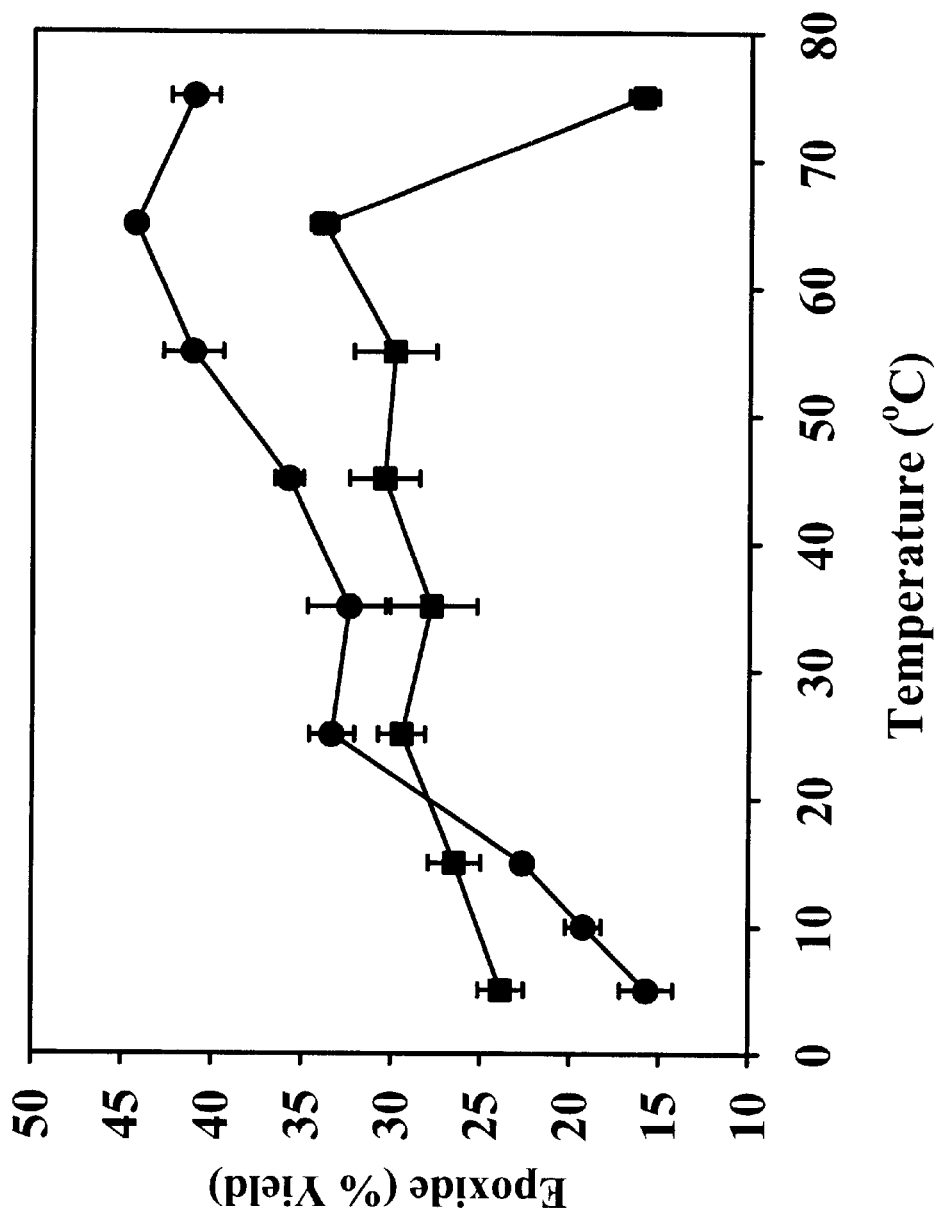
FIG. 5 shows the effect of temperature on the epoxidation of sodium oleate by peroxygenase bound on a Fluoropore membrane. Assays were conducted at pH 7.5 for t-butyl hydroperoxide (●) and pH 5.5 for $H_2O_2$ (■). Other assay conditions as in FIG. 4.

FIG. 5 shows the influence of temperature on the yield in one hour reactions. When the oxidant t-butyl hydroperoxide was used, the yield of epoxide increased as the temperature was increased to 65° C. and then decreased slightly at 75° C. The yield of epoxide at higher temperatures was the maximum possible given the amount of t-butyl hydroperoxide added. In contrast, increasing the temperature when hydrogen peroxide was the oxidant resulted in only modest increases in the epoxide yield, and at 75° C., the epoxide yield decreased. Note however that at 25° C., the yield of epoxide was approximately the same for both t-butyl hydroperoxide and hydrogen peroxide.

Larger scale reactions: Oat seeds and sodium oleate were increased twenty-fold. Readily available commercial filter holders could accommodate 142 mm (diameter) membranes. These are approximately nine-fold higher in area than the 42 mm membranes used for the smaller scale reactions. It was found that membrane clogging was a problem, and accordingly ways to reduce the particulate matter in the preparations was sought. The centrifugation force was gradually increased. After each increase, a portion was passed through a Fluoropore membrane, and this was tested for epoxidation activity. It was found that the centrifugation force could be increased from 9000×g to 16,000×g ($r_{average}$) without large losses in epoxidation activity. In addition, a prefiltration step with a 0.65 μm hydrophilic Durapore membrane was added, as our prior work has shown only minimal binding of peroxygenase to this membrane (Piazza, G. J., et al., Biotech. Lett., 22: 217–221 (2000)). As noted before, the addition of large amounts of oxidizing agent tends to diminish the activity of peroxygenase, and therefore during the preparation of epoxide the oxidizing agent was added in steps. Shown in Table 3 are the results of selected experiments with 100 mg sodium oleate and t-butyl hydroperoxide chosen to illustrate the trends that were observed.

TABLE 3

Larger Scale Production of Epoxide with t-Butyl Hydroperoxide and Hydrogen Peroxide

| Time (h) | Reaction A | Reaction B | Reaction C | Reaction D |
|---|---|---|---|---|
| | t-Butyl Hydroperoxide[a] or $H_2O_2$[b] Added (μmol) | | | |
| | 270 | 135 | 67.5 | 33.8 |
| 1 | 270 | 135 | 67.5 | 33.8 |
| 2 | 270 | 135 | 67.5 | 33.8 |
| 4 | 270 | 135 | 67.5 | 33.8 |
| 6 | 810 | 405 | 203 | 101 |
| Total | 1890 | 946 | 473 | 236 |

TABLE 3-continued

Larger Scale Production of Epoxide with t-Butyl Hydroperoxide and Hydrogen Peroxide

| | Reaction A | Reaction B | Reaction C | Reaction D |
|---|---|---|---|---|
| | Epoxide Yield at 24 h[c] (μmol) | | | |
| t-BuOOH | 191 | 258 | 262 | 230 |
| $H_2O_2$ | 33.9 | 42.0 | 74.9 | 108 |
| | Percent Yield Based on Sodium Oleate | | | |
| t-BuOOH | 58.2 | 78.4 | 79.5 | 69.8 |
| $H_2O_2$ | 10.0 | 12.8 | 22.8 | 33.0 |
| | Percent Yield Based on t-Butyl Hydroperoxide or $H_2O_2$ | | | |
| t-BuOOH | 10.1 | 27.3 | 55.4 | 97.4 |
| $H_2O_2$ | 1.7 | 4.4 | 15.8 | 45.8 |

[a]In addition to the indicated amount of t-butyl hydroperoxide, each reaction contained 100 mg sodium oleate (329 μmol), 32.4 mL 50 mM Hepes/0.1% Tween 20, pH 7.5, and peroxygenase immobilized on a 142 mm, 0.2 μm Fluoropore membrane; the reaction temperature was 25° C.
[b]In addition to the indicated amount of $H_2O_2$, each reaction contained 100 mg sodium oleate (329 μmol), 32.4 mL 50 mM acetate/50 mM MES/0.1% Tween 20, pH 5.5, and peroxygenase immobilized on a 142 mm, 0.2 μm Fluoropore membrane; the reaction temperature was 25° C.
[c]Results are the average of two repetitions.

In Table 3, at the lowest level of added oxidatant (Reaction D), the utilization of hydroperoxide was nearly quantitative, giving a 97.4% yield based upon hydroperoxide. However, when the amount of added t-butyl hydroperoxide was elevated (Reactions B and C) to achieve better conversion of sodium oleate, the yield of epoxide based upon sodium oleate could be increased only to about 80%, a yield similar to that achieved with 1 mg sodium oleate in our prior research with peroxygenase (Piazza, G. J., et al., Biotech. Lett., 22: 217–221 (2000)). As illustrated with Reaction A, further increases in t-butyl hydroperoxide diminished the yield of epoxide. When hydrogen peroxide was used as the oxidant, the highest yield of epoxide, 33% based on sodium oleate, was obtained at the lowest level of added hydrogen peroxide (Reaction D). As the level of added hydrogen peroxide was increased, the yield of epoxide gradually decreased. Thus hydrogen peroxide is highly toxic to peroxygenase.

In conclusion, the successful scale-up of peroxygenase catalyzed epoxidation has been achieved using t-butyl hydroperoxide as the oxidant. We expect that further increases in scale are likely using t-butyl hydroperoxide and other oxidants.

Epoxidation of styrene and cyclohexene: Reaction mixtures contained 1.9 mg (18.2 μmol) styrene or 1.5 mg (18.2 μmol) cyclohexene, 7.0 mL 50 mM Hepes/0.1% (w/v) Tween 20, pH 7.5, and peroxygenase immobilized on a 47 mm, 0.2 μm Fluoropore membrane. At 0, 1, 2, and 4 h, 3.34 μmol t-butyl hydroperoxide was added; at 6 h, 20.0 μmol t-butyl hydroperoxide was added. The reaction temperature was 25° C. At 24 h a sample was removed using a solid phase microextractor with a polydimethyl siloxane filter (100 μm thickness)(Supelco, Bellefonte, Pa.) and analyzed on an HP-MS 5890 GC/MS containing a 30 m HP-5MS column (Hewlett Packard, Palo Alto, Calif.). Epoxide yields shown below were obtained from separately prepared reaction:

| Styrene | Cyclohexene |
|---|---|
| (Percent Yield of Epoxide) | |
| 60.0 | 76.5 |
| 60.8 | 72.8 |

The above example shows that the peroxygenase can be a useful catalyst for epoxide formation in a wide variety of chemical substances besides lipid substrates.

All of the references and U.S. Patents cited herein are incorporated by reference in their entirety.

Thus, in view of the above, the present invention concerns (in part) the following:

A method for preparing membrane bound peroxygenase, said method involving (comprising, consisting essentially of, consisting of) grinding seeds containing peroxygenase to produce ground seeds, homogenizing the ground seeds in a buffer to form a slurry, centrifuging the slurry to produce a first supernatant, centrifuging the first supernatant to produce a second supernatant, and filtering the second supernatant through a protein-binding membrane filter to produce membrane bound peroxygenase.

The above method, further involving optionally filtering the second supernatant through a hydrophilic membrane filter prior to filtering the second supernatant through the protein-binding membrane filter.

The above method, wherein the seeds are oat, soybean, broad bean or mixtures thereof.

The above method, wherein the grinding involves grinding for about 20 to about 60 seconds.

The above method, wherein the homogenizing involves blending for about one to about two minutes.

The above method, wherein the buffer has a pH of about 7 (e.g., 0.1 M potassium phosphate buffer at pH 6.7).

The above method, wherein the centrifuging of the slurry and the first supernatant is at about 9,000 to about 16,000×g for about 10 minutes to about 15 minutes.

The above method, wherein the protein-binding membrane has a pore size of about 0.1 $\mu$m to about 2 $\mu$m.

Membrane bound peroxygenase prepared by the above method.

A method for the epoxidation of a compound having at least one carbon-carbon double bond, the method involving (comprising, consisting essentially of, consisting of) reacting a compound having at least one carbon-carbon double bond, a solvent, an oxidant, and membrane bound peroxygenase prepared by the above method.

The above method, wherein the solvent is an aqueous solvent having a pH from about 4.5 to about 9.5 or a nonpolar solvent.

The above method, wherein the oxidant is an organic hydroperoxide (e.g., t-butyl hydroperoxide or hydrogen peroxide).

The above method, wherein the reaction time is about one minute up to about seven days.

The above method, wherein the reaction time is about two hours to about 24 hours.

The above method, wherein the reaction time is about six hours to about 12 hours.

The above method, wherein the reaction temperature is about 5° C. to about 75° C.

The above method, wherein the reaction temperature is about 15° C. to about 65° C.

The above method, wherein the reaction temperature is about 15° C. to about 35° C.

The above method, further comprising isolating (recovering) the epoxidized compound.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A method for preparing membrane bound peroxygenase, said method comprising grinding seeds containing peroxygenase to produce ground seeds, homogenizing said ground seeds in a buffer to form a slurry, centrifuging said slurry to produce a first supernatant, centrifuging said first supernatant to produce a second supernatant, and filtering said second supernatant through a protein-binding membrane filter to produce membrane bound peroxygenase, wherein said protein-binding membrane bas a pore size of about 0.1 $\mu$m to about 2 $\mu$m.

2. The method according to claim 1, further comprising optionally filtering said second supernatant through a hydrophilic membrane filter prior to filtering said second supernatant through said protein-binding membrane filter.

3. The method according to claim 1, wherein said seeds are selected from the group consisting of oat, soybean, broad bean and mixtures thereof.

4. The method according to claim 1, wherein said grinding comprises grinding for about 20 to about 60 seconds.

5. The method according to claim 1, wherein said homogenizing comprises blending for about one to about two minutes.

6. The method according to claim 1, wherein said buffer has a pH of about 7.

7. The method according to claim 1, wherein said centrifuging of said slurry and said first supernatant is at about 9,000 to about 16,000×g for about 10 minutes to about 15 minutes.

8. The method according to claim 1, wherein said protein-binding membrane has a pore size of about 0.2 to about 1 $\mu$m.

\* \* \* \* \*